(12) United States Patent  (10) Patent No.: US 7,485,122 B2
Teoh  (45) Date of Patent: Feb. 3, 2009

(54) INTEGRATED ANCHOR COIL IN STRETCH-RESISTANT VASO-OCCLUSIVE COILS

(75) Inventor: Clifford Teoh, Los Altos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1194 days.

(21) Appl. No.: 10/185,671

(22) Filed: Jun. 27, 2002

(65) Prior Publication Data

US 2004/0002733 A1 Jan. 1, 2004

(51) Int. Cl.
*A61F 2/06* (2006.01)
(52) U.S. Cl. ...................................... 606/108
(58) Field of Classification Search ................. 606/108, 606/191, 198, 200, 157, 158
See application file for complete search history.

(56) References Cited

U.S. PATENT DOCUMENTS

| 3,174,851 A | 3/1965 | Buehler et al. |
| 3,351,463 A | 11/1967 | Rozner et al. |
| 3,753,700 A | 8/1973 | Harrison et al. |
| 4,561,439 A * | 12/1985 | Bishop et al. ............... 606/194 |
| 4,994,069 A | 2/1991 | Ritchart et al. |
| 5,122,136 A | 6/1992 | Guglielmi et al. |
| 5,226,911 A | 7/1993 | Chee et al. |
| 5,234,437 A | 8/1993 | Sepetka |
| 5,250,017 A | 10/1993 | Ariyoshi |
| 5,250,071 A | 10/1993 | Palermo |
| 5,261,916 A | 11/1993 | Engelson |
| 5,304,194 A | 4/1994 | Chee et al. |
| 5,304,195 A | 4/1994 | Twyford, Jr. et al. |
| 5,312,415 A | 5/1994 | Palermo |
| 5,350,397 A | 9/1994 | Palermo et al. |
| 5,354,295 A | 10/1994 | Guglielmi et al. |
| 5,382,259 A | 1/1995 | Phelps et al. |
| 5,522,836 A * | 6/1996 | Palermo ...................... 606/200 |
| 5,549,624 A | 8/1996 | Mirigian et al. |
| 5,582,619 A | 12/1996 | Ken |
| 5,690,666 A | 11/1997 | Berenstein et al. |
| 5,690,667 A * | 11/1997 | Gia ............................ 606/191 |
| 5,833,705 A | 11/1998 | Ken et al. |
| 5,853,418 A | 12/1998 | Ken et al. |
| 5,881,732 A | 3/1999 | Samson et al. |
| 5,941,888 A | 8/1999 | Wallace et al. |
| 5,964,771 A * | 10/1999 | Beyar et al. ................. 606/108 |
| 5,984,947 A | 11/1999 | Smith |
| 6,165,178 A * | 12/2000 | Bashiri et al. ............... 606/108 |
| 6,193,728 B1 | 2/2001 | Ken et al. |
| 6,280,457 B1 | 8/2001 | Wallace et al. |
| 6,361,558 B1 | 3/2002 | Hieshima et al. |
| 2001/0009996 A1* | 7/2001 | Ferrera et al. ................. 606/1 |
| 2001/0044633 A1* | 11/2001 | Klint ........................... 606/200 |
| 2002/0058962 A1 | 5/2002 | Wallace |

* cited by examiner

*Primary Examiner*—Eduardo C Robert
*Assistant Examiner*—Richard Shaffer
(74) *Attorney, Agent, or Firm*—Vista IP Law Group LLP (57) ABSTRACT

Vaso-occlusive devices are provided for occluding an aneurysm within the human vasculature. The vaso-occlusive device also includes a stretch-resisting member that extends through at least a portion of a lumen of the primary coil and is directly or indirectly attached to the primary coil at two locations axially separated from each other to prevent or minimize axial stretching of the primary coil. At one location, the stretch-resisting member is coupled to the primary coil via a flexible anchor assembly disposed within the lumen. The anchor coil is incorporated into the primary coil by disposing the anchor coil windings between the windings of the primary coil.

29 Claims, 9 Drawing Sheets

INTEGRATED ANCHOR COIL IN STRETCH-RESISTANT VASO-OCCLUSIVE COILS

RELATED APPLICATIONS

This application is related to copending application Ser. Nos. 10/185,650 and 10/185,669.

FIELD OF THE INVENTION

The field of the invention relates to implantable vaso-occlusive devices, and more particularly, to stretch-resistant vaso-occlusive coils.

BACKGROUND OF THE INVENTION

Vaso-occlusion devices are surgical implements or implants that are placed within the vasculature of the human body, typically via a catheter, to block the flow of blood through a vessel or an aneurysm stemming from the vessel via the formation of an embolus. One widely used vaso-occlusive device is a helical wire coil having windings that may be dimensioned to engage the walls of an aneurysm. Virtually all such vaso-occlusive implants are delivered by pushing the devices through wire-guided catheters.

As an example of an early vaso-occlusive device, U.S. Pat. No. 4,994,069, to Ritchart et al., describes a vaso-occlusive coil that assumes a linear helical configuration when stretched and a folded, convoluted configuration when relaxed. The coil assumes the stretched condition during delivery of the coil at the desired site by passage through the catheter, and assumes the relaxed configuration, which is better suited to occlude the aneurysm, once the device is so placed. Ritchart et al. describes a variety of secondary shapes, including "flower" shapes and double vortices. A random secondary shape is also described. Vaso-occlusive coils having little or no inherent secondary shape have also been described. For instance, in U.S. Pat. No. 5,690,666, to Berenstein et al., is found a coil having little or no shape after introduction into the vascular space.

Vaso-occlusive coils having materials added externally to the coil to enhance its therapeutic effect have also been manufactured. For example, vaso-occlusive coils having attached fibrous elements in a variety of secondary shapes are shown in U.S. Pat. No. 5,304,194. A vaso-occlusive coil with a fibrous woven or braided covering of a filamentary material is described in U.S. Pat. No. 5,382,259. And vaso-occlusive coils having a polymeric fiber wrapped around the wire of the primary coil or a polymeric covering wrapped around the primary shape of the coil are shown in U.S. Pat. No. 6,280,457.

There are a variety of ways of discharging shaped coils and linear coils into the human vasculature. In addition to those patents that apparently describe only the physical pushing of a coil out into the vasculature (e.g., Ritchart et al.), there are a number of other ways to release the coil at a specifically chosen time and site. U.S. Pat. No. 5,354,295 and its parent, U.S. Pat. No. 5,122,136, both to Guglielmi et al., describe an electrolytically detachable embolic device. In addition, a vaso-occlusive device with multiple detaching points was described in U.S. Pat. No. 5,941,888 to Wallace et al. A variety of mechanically detachable devices are also known, examples of which are disclosed in U.S. Pat. No. 5,234,437, to Sepetka, U.S. Pat. No. 5,250,071, to Palermo, U.S. Pat. No. 5,261,916, to Engelson, U.S. Pat. No. 5,304,195, to Twyford et al., U.S. Pat. No. 5,312,415, to Palermo, and U.S. Pat. No. 5,350,397, to Palermo et al.

Vaso-occlusive coils containing a means for preventing the stretching of the coil during movement of that coil are also known. For instance, in U.S. Pat. No. 5,833,705, to Ken et al., an implantable vaso-occlusive device is described in which a stretch-resisting member extends through the lumen of the outer helical coil and is attached to the coil at two locations. The stretch-resisting members can be made from polymeric filaments or other flexible materials. In U.S. Pat. No. 6,193,728, to Ken et al., a stretch-resistant vaso-occlusive coil is described in which the stretch-resisting member is indirectly attached to the coil via an anchor coil coaxially situated between the outer coil and the core wire. During manufacture of the coil assembly, which preferably involves the application of heat, care must be taken to avoid melting the polymeric filaments of the stretch-resisting member.

In another variation of the vaso-occlusive coil, instead of the anchor coil, a single twisted link, which has a loop at the distal end to connect with the stretch-resisting member, is utilized as the anchoring device in an attempt to distance the polymeric filament from the heated proximal end. Although this embodiment is successful in preventing the filament from melting, the single twisted link creates a stiff section at the proximal end of the coil. This stiff section can cause problems during placement of the coil in the aneurysm by preventing the proximal end from curving into the interior of the aneurysm. Rather, the stiff proximal end could extend through the mouth of the aneurysm into the parent artery where vaso-occlusion is not desired. In addition, the twisted anchor, with its relatively large diameter, is difficult to insert into vaso-occlusive coils with smaller lumens.

Accordingly, improved vaso-occlusive devices utilizing more flexible anchoring assemblies for the stretch-resisting member are desired.

SUMMARY OF THE INVENTION

The present inventions are directed to a vaso-occlusive device that can be deployed within the vasculature of a patient to occlude the flow of blood therein. Preferably, the inventive vaso-occlusive device is deployed to provide emboli in aneurysms located within the vasculatures of humans, but may also be used at any site in a human or animal that requires occlusion. In providing occlusion, the vaso-occlusive device includes a primary coil that can be deployed into one of any variety of secondary shapes to conform to the occlusion site. The inventive vaso-occlusive device can be carried to the target site using a delivery device and released therefrom using any one of a variety of detachable means, such as an electrolytic joint. The vaso-occlusive device also includes a stretch-resisting member that extends through at least a portion of a lumen located within the primary coil. The stretch-resisting member is directly or indirectly coupled to the primary coil to prevent or minimize axial stretching of the primary coil. At one of the locations, the stretch-resisting member is coupled to the primary coil via an anchor assembly disposed within the coil lumen. By way of non-limiting example, the anchor assembly can be located at the proximal end of the primary coil, and the stretch-resisting member can be affixed, either directly or indirectly, between the distal end of the primary coil or some other location on the primary coil and the proximally located anchor assembly.

In accordance with a first aspect of the invention, the anchor assembly comprises one or more flexible joints. In the preferred embodiment, the anchor assembly also comprises a plurality of rigid members between which the flexible joints are disposed. For example, if the anchor assembly includes first and second rigid members, a single flexible joint may be located therebetween. The first rigid member may be directly or indirectly coupled to the outer primary coil and the second rigid member may be directly or indirectly coupled to the stretch-resisting member.

Although the present invention should not necessarily be limited by this advantage, the presence of the flexible joint(s) provide the desired flexibility for the proximal end of the primary outer coil, while also having a sufficient length to locate the stretch-resisting member away from any heat generated at the proximal end of the primary coil during the manufacturing process. By way of non-limiting example, the rigid members may be an anchor member (such as, e.g., a tubular member or anchor coil) and a link. The anchor assembly may also comprise a chain of links, each of which is twisted in order to maintain the axial strength of the anchor assembly. But the invention in its broadest sense should not be limited to an anchor coil and link or a chain of twisted links.

In accordance with a second aspect of the invention, the anchor assembly comprises an anchor coil and a link directly or indirectly coupled between the anchor coil and the stretch-resisting member. By way of non-limiting example, the distal and proximal ends of the stretch-resisting member can be respectively affixed to the distal end of the primary coil and the link. Filler material, such as, e.g., polyethyleneterephthalate (PET), polyamide, silicon, or polyurethane can be used to provide structural integrity to the proximal end of the primary coil where the anchor coil is affixed within the primary coil lumen. The link can be composed of any suitable biocompatible material, but in the preferred embodiment, platinum is used.

Although the present inventions should not necessarily be limited by this advantage, the presence of the link allows the stretch-resisting member to be located away from any heat generated at the proximal end of the primary coil during the manufacturing process. The flexible connection between the anchor coil and the link, provide the desired flexibility for the proximal end of the primary coil. By way of non-limiting example, the length of the anchor coil, having a preferable length of 1.0 mm, and link combination can be reduced to about 1.8 mm from 2.6 mm. The length of the link can be less than 1 mm.

In accordance with a third aspect of the invention, the anchor assembly comprises an anchor chain comprising a proximal twisted link and a distal twisted or untwisted link, which is directly or indirectly coupled to the stretch-resisting member. The presence of the distal link allows the length of the proximal twisted link to be reduced, while locating the stretch-resisting member away from any heat generated at the proximal end of the primary coil during the manufacturing process. The reduction in the length of the relatively stiff proximal link, and the flexible connection between the proximal link and the distal link, provide the desired flexibility for the proximal end of the primary coil. By way of non-limiting example, the distal and proximal ends of the stretch-resisting member can be respectively affixed to the distal end of the primary coil and the distal link. By way of non-limiting example, a proximal twisted link having a preferable length of 2.6 mm can be reduced to about 1.2 mm, while the length of the distal link can be less than 1 mm. In the preferred embodiment, the anchor chain only includes the proximal and distal links, but can include additional links as well depending on the desired flexibility and length of the anchor chain. Filler material, such as, e.g., PET, polyamide, silicon, or polyurethane, can be used to provide structural integrity to the proximal end of the primary coil where the proximal link may be affixed within the primary coil lumen in the absence of an anchor coil. The anchor chain can be composed of any suitable biocompatible material, but in the preferred embodiment, platinum is used.

Although the present inventions should not necessarily be limited by this advantage, the presence of an anchor chain eliminates the need for a single piece proximal anchor, e.g., an anchor coil, or at the least, allows the length of the anchor coil to be reduced, while locating the stretch-resisting member away from any heat generated at the proximal end of the primary coil during the manufacturing process. The elimination or reduction in the length of the relatively stiff anchor coil, and the flexible connections formed by the anchor chain, provide the desired flexibility for the proximal end of the primary coil. By way of non-limiting example, a 2.6 mm single piece proximal anchor can be replaced with a 2.4 mm anchor chain, with each of the proximal and distal links being about 1.2 mm. The lengths of the respective proximal and distal links, however, need not be the same. For example, the distal link can be smaller than the proximal link.

In accordance with a fourth aspect of this invention, the anchor assembly comprises a helical structure directly or indirectly coupled to the stretch-resisting member. In the preferred embodiment, the helical structure takes the form of an anchor coil. Other types of helical structures, such as threads on a cylindrical element, can also be used. By way of non-limiting example, the proximal end of the stretch-resisting member can be respectively affixed to the distal end of the anchor coil. The anchor coil is fixedly coupled to the outer coil by situating the windings of the anchor coil between the windings of the primary coil. In the case of a threaded cylindrical element, the threads are situated between the winding of the primary coil. In the preferred embodiment, each of the windings of the anchor coil can be disposed between adjacent windings of the primary coil. Alternatively, multiple windings, e.g., a winding pair, of the anchor coil can be disposed between adjacent windings of the primary coil. Even more alternatively, multiple windings of the primary coil can be disposed between adjacent windings of the anchor coil.

There are a variety of ways that the anchor coil and primary coil can be formed and incorporated into the vaso-occlusive device. For ease of assembly and to minimize the exertion of axial stress on the windings of the anchor and primary coils, the windings of the anchor and primary coils can be open-pitched. For example, a preferred method comprises making the outer primary coil by winding a first wire into a first helical coil so that the proximal end of the first helical coil has open-pitched windings, and making the anchor coil by winding a second wire into a second helical coil so that the second helical coil has open-pitched windings. The anchor coil is then incorporated into the primary coil, e.g., screwing, such that the open-pitched windings of the anchor coil are disposed between adjacent open-pitched windings of the primary coil.

In the preferred embodiment, the entirety of the anchor coil has open-pitched windings. It should be noted, however, that only the distal end of the anchor coil or otherwise the portion of the anchor coil that is incorporated into the primary coil may have the open-pitched windings. The windings of the anchor coil can be single winding open pitched, double winding open pitched, or any other multiple-winding open pitched. Alternatively, the windings of the primary coil can be single winding open pitched, double winding open pitched, or any other multiple-winding open pitched. The distal end of the anchor coil may be tapered to facilitate incorporation into the primary coil.

Although the present invention should not necessarily be limited by this advantage, the incorporation of the anchor coil into the primary coil decreases the wall thickness of the proximal end of the vaso-occlusive device, thereby providing the desired flexibility for the proximal end of the primary outer coil, while also locating the stretch-resisting member away from any heat generated at the proximal end of the anchor coil during the manufacturing process.

In accordance with a fifth aspect of this invention, the vaso-occlusive device includes a plurality of primary coils, a plurality of stretch-resisting members extending through at least portions of the respective primary coils, and one or more detachable joints located between adjacent primary coils. The distal and proximal ends of the stretch-resisting member can be respectively affixed to anchor assemblies, such as, e.g., those previously described, located at one or both of the distal and proximal ends of each primary coil.

Although the present inventions should not necessarily be limited by this advantage, the presence of multiple detachment means allows for the deployment of vaso-occlusive devices with selectable length. This enables physicians to select the length of the deployed vaso-occlusive device as desired in light of the condition and size of the aneurysm being treated. The use of anchor assemblies to couple the stretch-resisting member to the primary outer coil segments allows the stretch-resisting member to be located away from any heat generated at the proximal end of the primary coil during the manufacturing process.

BRIEF DESCRIPTION OF THE FIGURES

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not, therefore, to be considered limiting of its scope, the invention will be described and explained with additional specificity and detail through the use of the accompanying drawings in which.

DETAILED DESCRIPTION OF THE PREFERRED EMBODIMENTS

Figure 1:
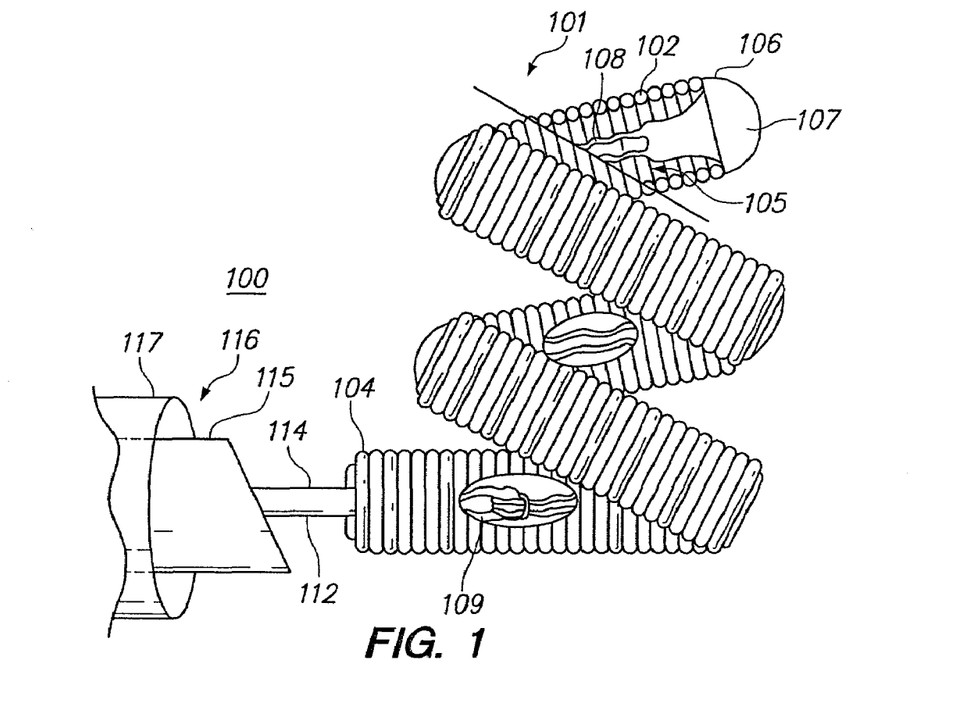
FIG. 1 shows a side view, partial cutaway of a vaso-occlusive assembly constructed in accordance with a preferred embodiment of the present inventions.

Referring to FIG. 1, a vaso-occlusive assembly 100 constructed in accordance with one preferred embodiment is illustrated. The vaso-occlusive assembly 100 includes a delivery device 116 comprising a core wire 114 disposed within an elongate tubular catheter 117, and a vaso-occlusive device 101 detachably associated with the distal end of the delivery device 116 via use of detachable means 112 formed at the end of the core wire 114. In the illustrated embodiment, the detachable means 112 is an electrolytic severable joint, as will be described in further detail below. Other types of detachable means, such as mechanical, can be used to connect the vaso-occlusive assembly 100 to various other delivery devices. Thus, it can be appreciated that the vaso-occlusive device 101 can be associated with delivery devices other than those that use core wires.

The vaso-occlusive device 101 includes an outer primary coil 102, which has a proximal end 104, a distal end 106, and a lumen 105 extending therethrough between the proximal and distal ends 104 and 106. The vaso-occlusive device 101 further includes a stretch-resisting member 108, which extends through the coil lumen 105 and is secured to the primary coil 102 at two locations to prevent axial stretching of the primary coil 102. Specifically, the proximal and distal ends of the stretch-resisting member 108 are respectively affixed to the proximal and distal ends 104 and 106 of the primary coil 102. Alternatively, the stretch-resisting member 108 only extends through a portion of the lumen and is attached to the primary coil 102 at a location between the proximal and distal ends 104 and 106 of the primary coil 102.

The distal end of the stretch-resisting member 108 may be secured to the coil 102 by melting, gluing, or otherwise fixedly attaching the stretch-resisting member 108 to the coil 102, either at the distal end 106 or some location between the ends of the coil 102. In the illustrated embodiment, the distal end of the stretch-resisting member is glued or melted and reformed into a distal cap 107, the diameter of which is larger than the inner diameter of the coil 102. Alternatively, the stretch-resisting member 108 may be tied in a knot (not shown), which may or may not be attached to the primary coil 102. These methods of attachment are disclosed in more detail in U.S. Pat. No. 5,582,619, the entirety of which is herein expressly incorporated by reference. At the proximal end 104, the vaso-occlusive device 101 includes an anchor assembly 109 mounted within the lumen 105. The proximal end of the stretch-resisting member 108 is indirectly attached to the proximal end 104 of the primary coil 102 through the anchor assembly 109. The anchor assembly 109 comprises a plurality of rigid members and one or more flexible joints that are situated between the rigid members to provide flexibility to the proximal end 104 of the vaso-occlusive device 101 while maintaining separation between the stretch-resisting member 108 and the proximal end 104 of the primary coil 102. As will be described in further detail below, the rigid members of the anchor assembly 109 may comprise an anchor coil with an attached link or a chain of links, both of which advantageously maintain the flexibility of the proximal end 104. It should be noted that for the purposes of this specification, a "flexible joint" is any joint the location at which the anchor assembly 109 will tend to bend in the presence of a transversely applied force.

In one preferred embodiment, the vaso-occlusive device 101 is adapted to accept the electrolytically severable joint 112. The delivery device 116 in this variation has, except for the severable joint 112 that is intended to be the site of electrolysis, an insulating layer 115 that is disposed on and continued to the end of the core wire 114 where it connects with the coil device 101. The insulating layer 115 may be polytetrafluoroethylene (e.g., Teflon), polyparaxylxylene (e.g., Parylene), polyethyleneterephthalate (PET), polybutyleneterephthalate (PBT), cyanoacrylate adhesives, or other suitable insulating layer, but preferably is polymeric, and most preferably is Teflon. The electrolytically severable joint is discussed in detail in U.S. Pat. No. 5,354,295 and its parent, U.S. Pat. No. 5,122,136, both patents to Guglielmi and Sepetka, described above, and herein expressly incorporated by reference. It should be noted that other mechanisms for detaching the vaso-occlusive coil may be used. For example, the vaso-occlusive device may be mechanically deployed. Various mechanical mechanisms are described in U.S. Pat. Nos. 5,234,437; 5,250,071; 5,261,916; 5,304,195; 5,312,415; and 5,350,397, the entirety of which are herein expressly incorporated by reference.

The materials used in constructing the primary coil 102 may be any of a wide variety of materials, and preferably, a radio-opaque material such as a metal or a polymer. Suitable metals and alloys for the wire making up the primary coil 102 include the Platinum Group metals, especially platinum, rhodium, palladium, rhenium, as well as tungsten, gold, silver, tantalum, and alloys of these metals. In addition to being largely biologically inert, these metals have significant radio-opacity and their alloys may be tailored to accomplish an appropriate blend of flexibility and stiffness. Highly preferred is a platinum/tungsten alloy, e.g., 8% tungsten and the remainder platinum.

The primary coil 102 may also be made of radiolucent fibers or polymers (or metallic threads coated with radiolucent or radio-opaque fibers) such as Dacron (polyester), polyglycolic acid, polylactic acid, fluoropolymers (polytetrafluoroethylene), Nylon (polyamide), or even cotton or silk. If a polymer is used as the major component of the primary coil 102, it is desirably filled with some amount of radio-opaque material such as powdered tantalum, powdered tungsten, bismuth oxide, barium sulfate, and the like.

When manufacturing the primary coil 102, the coil material is wound into a coil, which will typically be linear. Generally speaking, when the coil 102 is a metallic coil made from a platinum alloy or a super-elastic alloy such as titanium/nickel alloy, known as "nitinol". The diameter of the wire used in the production of the coils is preferably in the range of 0.00025 and 0.006 inches. The coil preferably has a primary diameter of between 0.003 and 0.025 inches, but for most neurovascular applications, a diameter between 0.008 to 0.018 inches provides sufficient hoop strength to hold the primary coil 102 in place within the chosen body site, lumen, or cavity, without substantially distending the wall of the site and without moving from the site as a result of the repetitive fluid pulsing found in the vascular system.

The axial length of the coil wire will usually fall in the range of 0.5 to 100 cm, more usually 2.0 to 40 cm. Depending upon usage, the coil may well have 10-75 turns per centimeter, preferably 10-40 turns per centimeter. All of the dimensions here are provided only as guidelines, and the invention, in its broader aspects, should not be limited thereto. Only dimensions that are suitable for use in occluding sites within the human body, however, are included in the scope of this invention.

Depending on the desired therapeutic effect and the shape of the site to be treated, the primary coil 102 may later be treated or accessorized in numerous ways in order to enhance its therapeutic effect. The primary coil 102 may be made to form various secondary shapes, often through the use of heat treatment, that may be better suited to fill a particular treatment site, as disclosed in U.S. Pat. Nos. 5,853,418 and 6,280,457, the entireties of which are expressly incorporated herein by reference. Alternatively, the coil 102 may have little or no shape after introduction into the vascular space, as disclosed in U.S. Pat. No. 5,690,666, the entirety of which is expressly incorporated by reference herein. In addition, external materials may be added to the outside of the primary coil 102 in an effort to increase its thrombolytic properties. These alternative embodiments are disclosed in U.S. Pat. Nos. 5,226,911; 5,304,194; 5,549,624; and 5,382,259; the entireties of which are expressly incorporated herein by reference, and U.S. Pat. No. 6,280,457, the entirety of which has previously been incorporated by reference.

In a preferred embodiment, the stretch-resisting member 108 is fibrous and desirably polymeric. Suitable polymeric materials can be either thermosetting or thermoplastic and can comprise a bundle of threads or a single filament. Thermoplastics are preferred because they allow simplification of the procedure for constructing the assembly 100 since they may be melted and formed into the distal cap 107. Simple tools, such as soldering irons, may be used to form the distal cap 107. Thermosetting plastics would typically be held in place by an adhesive. Suitable polymers include most biocompatible materials that may be made into fibers, including thermoplastics, e.g., polyesters such as polyethyleneterephthalate (PET), especially Dacron; polyamides, including the Nylons; polyolefins, such as polyethylene, polypropylene, polybutylene, their mixtures, alloys, block, and random copolymers; polyglycolic acid; polylactic acid; fluoropolymers (polytetrafluoroethylene) or even silk or collagen. The stretch-resisting polymer may be made from materials used as dissolvable sutures, for instance, polylactic acid or polyglycolic acid, to encourage cell growth in the aneurysm after their introduction. Highly preferred is polypropylene, for instance, in the form of 10-0 and 9-0 polypropylene suture material. The diameter of the polymer is typically between about 0.0001 inches and about 0.01 inches.

In some variations of the invention, the stretch-resisting member 108 may be composed of any of a wide variety of stainless steels if some sacrifice of radio-opacity and flexibility can be tolerated. Stretch-resisting members of this type are described in U.S. Pat. No. 5,853,418. Very desirable materials of construction, from a mechanical point of view, are materials that maintain their shape despite being subject to high stress. Certain "super-elastic alloys" include various nickel-titanium alloys (48-58 atomic % nickel and optionally containing modest amounts of iron); copper/zinc alloys containing 1-10 weight % of beryllium, silicon, tin, aluminum, or gallium; or nickel/aluminum alloys (36-38 atomic % aluminum). Particularly preferred are the alloys described in U.S. Pat. Nos. 3,174,851; 3,351,463; and 3,753,700. Especially preferred is nitinol. These are very sturdy alloys that will tolerate significant flexing without deformation even when used as very small diameter wire. If a super-elastic alloy such as nitinol is used in the stretch-resisting member 108, the diameter of the wire may be significantly smaller than that used when the relatively more ductile platinum or platinum/tungsten alloy is used as the material of construction.

Figure 2A:
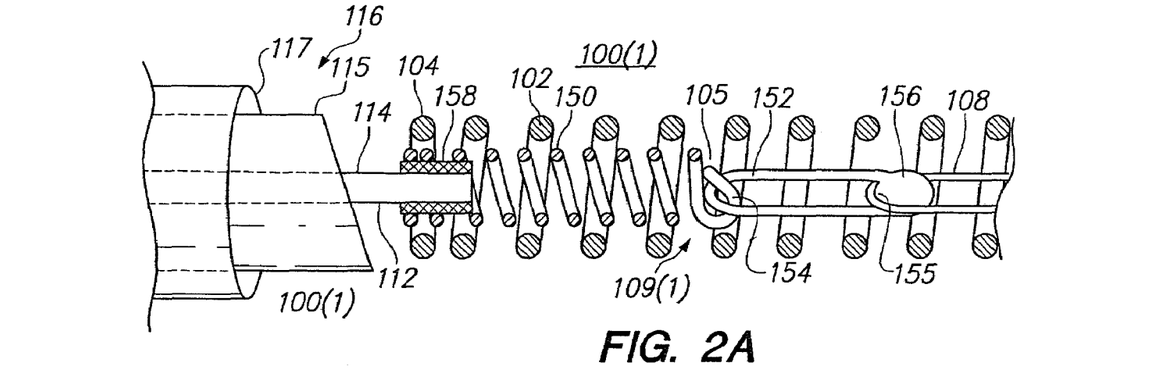
FIG. 2A shows a longitudinal sectional view of the vaso-occlusive assembly of FIG. 1, particularly showing one embodiment of an anchor assembly constructed in accordance with the present inventions.

In one preferred embodiment of a vaso-occlusive device 101(1), as seen in FIG. 2A, the stretch-resisting member 108 is connected indirectly to the proximal end 104 of the primary coil 102 through an anchor assembly 109(1), comprising an anchor coil 150 and an attached link 152. The anchor coil 150 is coaxially situated in the coil lumen 105. In the illustrated embodiment, the anchor coil 150 is preferably less than 2.6 mm long, preferably about 1.0 mm long.

A loop 154, formed from the final turn or half-turn of the anchor coil 150, is connected to the link 152, which is then connected to the stretch-resisting member 108. The stretch-resisting member 108 may be attached to the link 152 through any appropriate means, including looping the stretch-resisting member 108 through or around the additional link 152 or tying the stretch-resisting member 108 to the link 152. The link 152 is sealed by heating/welding the wire to close the loop, preferably forming a ball 156 at the sealed junction 155. Alternatively, the link 152 may be laser cut. In the illustrated embodiment, the link 152 may be shorter in length than the anchor coil 150, preferably less than 1 mm, e.g., about 0.8 mm long. The link 152 can be made of the same materials used to make the primary coil 102, including the Platinum Group metals, especially platinum, rhodium, palladium, rhenium, as well as tungsten, gold, silver, tantalum, and alloys of these metals. Suitable polymers may also be used. These include most biocompatible materials that may be made into fibers, including thermoplastics, e.g., polyesters such as Dacron; polyamides, including the Nylons; polyolefins, such as polyethylene, polypropylene, polybutylene, their mixtures, alloys and block. The relatively short anchor coil 150 and the corresponding flexible connection between the anchor coil 150 and the link 152, provide for additional flexibility of the primary coil 102 at the proximal end 104.

In this preferred embodiment, a filler material 158 is placed in the coil lumen 105 for stabilization and to attach the primary coil 102 to the core wire 114. The filler material 158 preferably comprises a thermoplastic formed into place or an epoxy or the like and adheres in turn to both the anchor assembly 109(1) and the core wire 114. Preferably, the filler material 158 is insulative. The filler material 158 preferably comprises PET, polyamide, silicon, or polyurethane. The core wire 114 is attached to the vaso-occlusive device 101(1) by inserting the distal tip of the core wire 114 into the filler material 158.

Figure 2B:
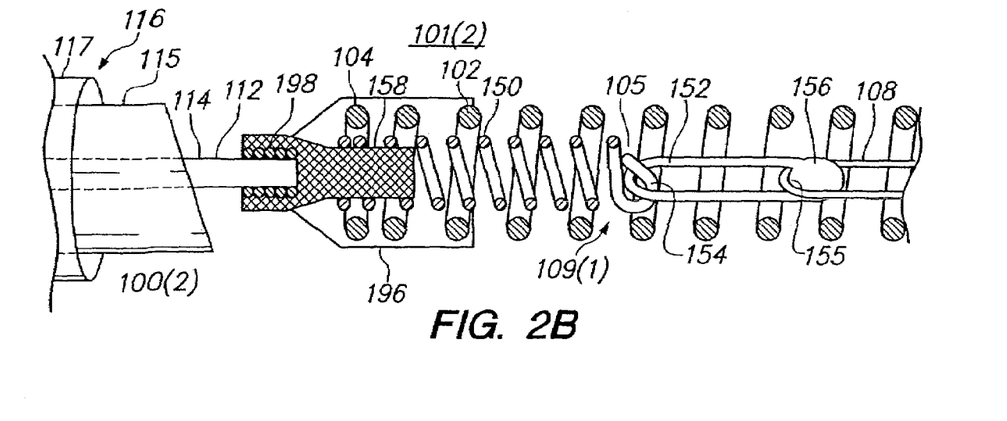
FIG. 2B shows a longitudinal sectional view of the vaso-occlusive assembly of FIG. 1, particularly showing another embodiment of an anchor assembly constructed in accordance with the present inventions.

Turning to FIG. 2B, in an alternative embodiment of a vaso-occlusive device 101(2), a bushing 196 is used to couple the core wire 114 to the primary coil 102. Specifically, the proximal end of the primary coil 102 is mounted within the distal end of the bushing 196, and the distal end of the core wire 114 is disposed within a mini coil 198, which in turn, is mounted within the proximal end of the bushing 196. The filler material 158 is disposed in the proximal end of the lumen of the primary and anchor coils and surrounds the core wire 114. The mini coil 198 provides additional physical mass obstruction to which the filler material 158 can adhere, thereby maintaining the tensile strength of the main junction between the primary coil 102 and the detachment means 112.

Figure 2C:
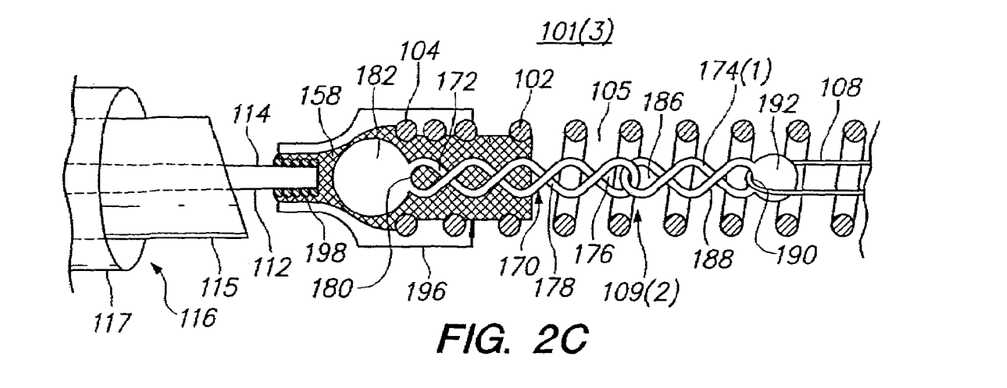
FIG. 2C shows a longitudinal sectional view of the vaso-occlusive assembly of FIG. 1, particularly showing another embodiment of an anchor assembly constructed in accordance with the present inventions.

Referring to FIG. 2C, in another preferred embodiment of a vaso-occlusive device 101(3), the stretch-resisting member 108 is indirectly attached to the primary coil 102 through an anchor assembly 109(2) comprising an anchor chain 170 with two links, a proximal link 172 and a distal link 174(1). The links may be in any form, e.g., twisted or intersecting, that prevents the links from collapsing on themselves such that the stretch-resisting member 108 is separated from the proximal end 104 and is not melted or otherwise damaged during the manufacturing of the coil assembly 100.

In the preferred embodiment illustrated in FIG. 2C, the proximal link 172 is twisted. The proximal twisted link 172 is formed by twisting a wire around itself and includes a closed loop 176 at its distal end, at least one twist/intersection 178, and a sealed junction 180 in which the two ends of the wire have been melted together. In a preferred embodiment, a ball 182 that is formed at the sealed junction 180 as a result of the melting process is used to increase tensile strength of the main junction between the primary coil 102 and the detachment means 112. In the illustrated embodiment, the proximal link 172 is less than about 2.6 mm, preferably about 1.2 mm in length.

In this preferred embodiment, a bushing 196 is used to couple the core wire 114 to the primary coil 102. Specifically, the proximal end of the primary coil 102 is mounted within the distal end of the bushing 196. The core wire 114 is mounted in the proximal end of the bushing in a manner similar to that discussed with reference to FIG. 2B. The ball 182, located just distal of the proximal end 104 or the primary coil 102, is also contained within the bushing 196, surrounded by filler material 158. As with the mini coil 198, the ball 182 provides additional physical mass obstruction to which the filler material 158 can adhere, thereby maintaining the tensile strength of the main junction between the primary coil 102 and the detachment means 112. In an alternative embodiment, the proximal end of the primary coil 102 may be crimped around the base of the ball 182 (not shown), thereby increasing the tensile strength of the anchor.

In the embodiment illustrated in FIG. 2C, the distal link 174(1) is also twisted, which like the proximal link 172, is formed by twisting a wire around itself and includes a closed loop 186, at least one twist/intersection 188, and a sealed juncture 190 in which the two ends of the wire have been melted together. A ball 192 is formed at the sealed junction as a result of the melting process. In the illustrated embodiment, the distal link 174(1) is shorter than the proximal link 172, preferably about 0.8 mm long. The distal link 174(1) may be connected to the proximal link 172 by interconnecting or looping together their closed loops 176 and 186, forming a flexible joint in the anchor assembly 109(2). The stretch-resisting member 108 is attached to the distal link 174(1) through any appropriate means, including looping the stretch-resisting member 108 through or around the distal link 174(1) or tying the stretch-resisting member 108 to the distal link 174(1).

The links 172, 174 may be made from the same material used to make the vaso-occlusive coil 102, including the Platinum Group metals, especially platinum, rhodium, palladium, rhenium, as well as tungsten, gold, silver, tantalum, and alloys of these metals. Suitable polymers may also be used. These include most biocompatible materials that may be made into fibers, including thermoplastics, e.g., polyesters such as Dacron; polyamides, including the Nylons; polyolefins, such as polyethylene, polypropylene, polybutylene, their mixtures, alloys and block. Although only two links are depicted in FIG. 2C, additional links may be inserted between the distal 174 and proximal 172 links as desired. The anchor chain 109(2) formed from the links 172, 174 provides for a more flexible means to attach the stretch-resisting member 108 indirectly to the vaso-occlusive coil 102.

In this preferred embodiment, a bushing 196 is used to couple the core wire 114 to the primary coil 102. The proximal end of the primary coil 102, with the ball joint 182 extending therefrom, is mounted within the distal end of the bushing 196, and the distal end of the core wire 114 is disposed within a mini coil 198, which in turn, is mounted within the proximal end of the bushing 196. The filler material 158 is disposed within the coil lumen 105 surrounding the proximal end of the proximal link 172 and around the ball joint 182 and mini coil 198 to stabilize and enhance the structural integrity of the junction between the detachment means and the vaso-occlusive coil device 101(3).

Figure 2D:
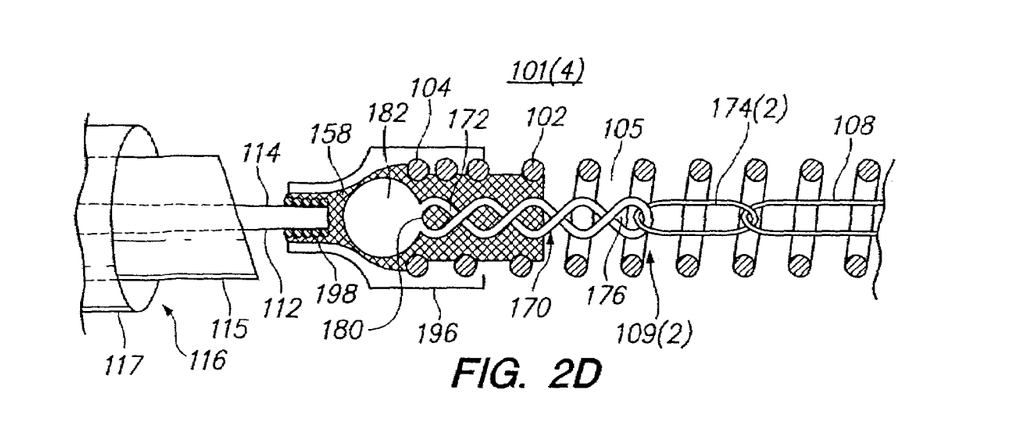
FIG. 2D shows a longitudinal sectional view of the vaso-occlusive assembly of FIG. 1, particularly showing another embodiment of an anchor assembly constructed in accordance with the present inventions.

Although the distal link 174(1) of the anchor assembly 109(2) is shown as being twisted, an untwisted distal link can be used. For example, referring to FIG. 2D, an anchor assembly 109(3) of a vaso-occlusive device 101(4) uses an untwisted distal link 174(2). Similar to the embodiment described in FIG. 2A, the distal link 174(2) may be formed by heating/welding the wire to close the loop, or it may be a laser cut piece. As depicted in FIG. 2D, the distal link 174(2) is shorter than the proximal link 172, preferably about 0.8 mm long. The distal link 174(2) can be composed of the same material and can be connected to the proximal link 172 and stretch-resisting member 108 in the same manner as described with respect to the distal link 174(1) in vaso-occlusive device 101(3).

Figure 3:
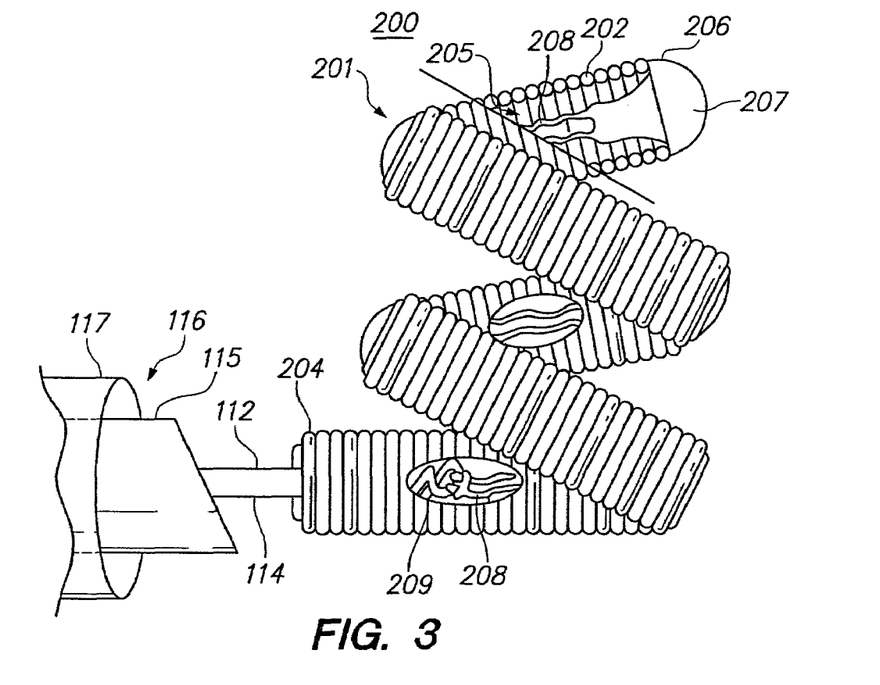
FIG. 3 shows a side view, partial cutaway of a vaso-occlusive assembly constructed in accordance with another preferred embodiment of the present inventions.

Referring to FIG. 3, a vaso-occlusive assembly 200 constructed in accordance with another preferred embodiment is described. Like the afore-described vaso-occlusive assembly 100, the assembly 200 includes the elongate delivery device 116, which includes the detachable means 112 and associated slidable core wire 114. The assembly 200 differs in that it includes a vaso-occlusive device 201 with a different anchoring assembly. The device 201 includes an outer primary coil 202, which has a proximal end 204, a distal end 206, and a lumen 205 extending therethrough. The vaso-occlusive device 201 further includes a stretch-resisting member 208, which extends through the coil lumen 205 and is secured to the primary coil 202 at two locations to prevent axial stretching of the primary coil 202. Specifically, the proximal and distal ends of the stretch-resisting member 208 are respectively affixed to the distal and proximal ends 102 and 104 of the primary coil 202. Alternatively, the proximal and distal ends of the stretch-resisting member 208 may be attached to one or more locations between the proximal and distal ends 204 and 206 of the primary coil 202. At the proximal end 204, the vaso-occlusive device 201 includes an anchor assembly 209 fixedly coupled to the primary outer coil 202. The proximal end of the stretch-resisting member 208 is indirectly attached to the proximal end 204 of the outer coil 202 through the anchor assembly 209, and specifically, an anchor coil 232 (shown in alternative embodiments of FIGS. 4B and 4D as 232(1) and 232(2). As will be described in further detail below, the anchor coil 232 is mated with the primary coil 202, such that windings of the anchor coil 232 are disposed in the space between adjacent windings of the primary coil 202.

The primary coil 202, anchor coil 232, and stretch-resisting member 208 can be composed of the same material and constructed in the same manner previously described with respect to the corresponding elements in the vaso-occlusive device 101. The distal end of the stretch-resisting member 208 can be fixedly attached to the coil 202 as previously described in the device 101, e.g., by reforming the distal end of the stretch-resisting member 208 into a distal cap 207 or by attaching the stretch-resisting member to some other location on the coil using any appropriate means.

Figure 4A:
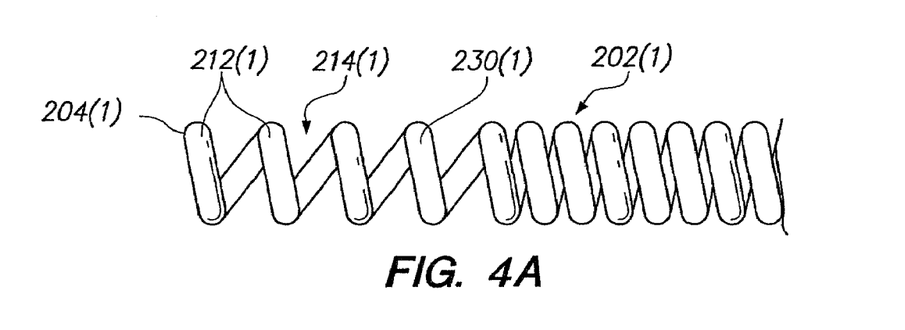
FIG. 4A shows a side view of one embodiment of a primary coil that can be used in the anchor assembly of FIG. 5A.
Figure 4B:
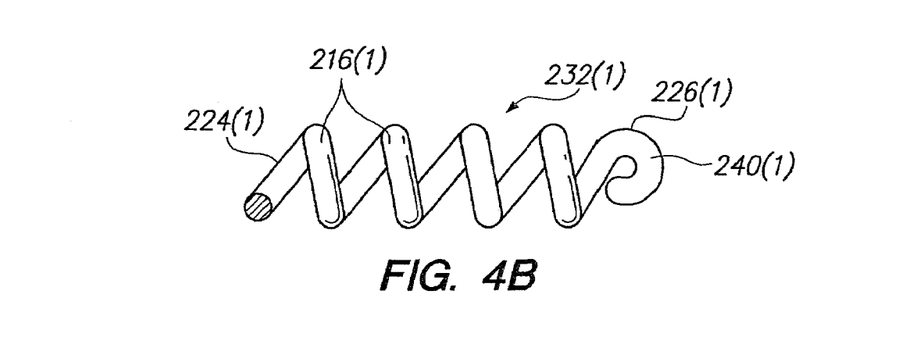
FIG. 4B shows a side view of one embodiment of an anchor coil that can be used in the anchor assembly of FIG. 5A.
Figure 4C:
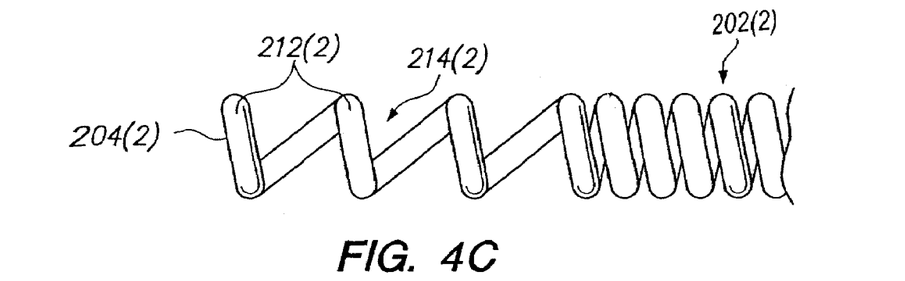
FIG. 4C shows a side view of one embodiment of a primary coil that can be used in the anchor assembly of FIG. 5B.

Referring to FIGS. 4A-4D, the primary coil 202 (shown in alternative embodiments of FIGS. 4A and 4C as 202(1) and 202(2)) is similar to the primary coil 102 used in the other preferred embodiments depicted in FIGS. 2A and 2B, except that the proximal end 204 of the primary coil 202 is made to have an open pitch. The open pitch at the proximal end 204 enables windings 216 from the anchor coil 232 (shown in alternative embodiments of FIGS. 4B and 4D as 232(1) and 232(2)) to be incorporated in the space 214 (shown in alternative embodiments of FIGS. 4A and 4C as 214(1) and 214(2)) between consecutive windings 212 (shown in alternative embodiments of FIGS. 4A and 4C as 212(1) and 212(2)) of the primary coil 202. The spacing of the windings 212 at the proximal end 204 depends on the number and thickness of windings 216 of the anchor coil 232 that will be disposed within each of the spaces 214.

Figure 4D:
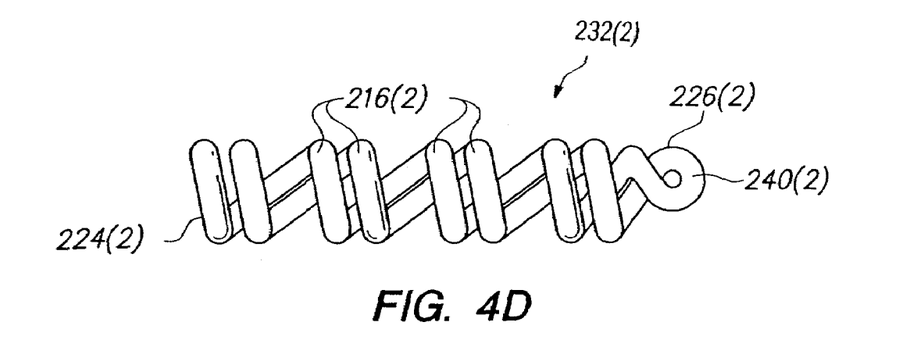
FIG. 4D shows a side view of one embodiment of an anchor coil that can be used in the anchor assembly of FIG. 5B.

Generally speaking, the anchor coil 232 is made such that it is similar in size (diameter) and properties to the outer primary coil 202. The length of the anchor coil 232 can be varied without sacrificing mechanical properties or performance in order to separate the stretch-resisting member 208 sufficiently from the proximal end during manufacture. In the illustrated embodiment, the anchor coil 232 is about 2 mm long.

In the preferred embodiment, the windings 212 of the proximal end 204 of the primary coil 202 are spaced such that they conveniently accommodate the size and number of the windings 216 of the anchor coil 232 without exerting a substantial axial stress to the windings of the primary coil 202 and anchor coil 232.

For example, as illustrated in FIGS. 4A and 4B, an anchor coil 232(1) has a single winding open pitch, and windings 212(1) on a primary coil 202(1) are spaced to accommodate a single winding 216(1) of the anchor coil 232(1), such that each winding 216(1) of the anchor coil 232(1) easily fits between adjacent windings 212(1) of the primary coil 202(1). A loop 240(1) formed from the final turn or half-turn of the anchor coil 232(1) is connected to the stretch-resisting member 208.

As another example, as depicted in FIGS. 4C and 4D, an anchor coil 232(2) formed by one strand of wire has a double winding open pitch, and the windings 212(2) on a primary coil 202(2) are spaced to accommodate a double winding 216(2) of the anchor coil 232(2), such that each double winding 216(2) of the anchor coil 232(2) easily fits between adjacent windings 212(2) of the primary coil 202(2). A loop 240(2) formed from the final turn or half-turn of the anchor coil 232(2) provides the threaded loop for the stretch-resisting member 208.

Although only anchor coils having single and double winding open pitches have been described, anchor coils of other varying thickness and pitch may be incorporated where the proximal end of the outer coil has been formed such that the spacing between adjacent windings can accommodate the size and number of the anchor coil windings.

Figure 5A:
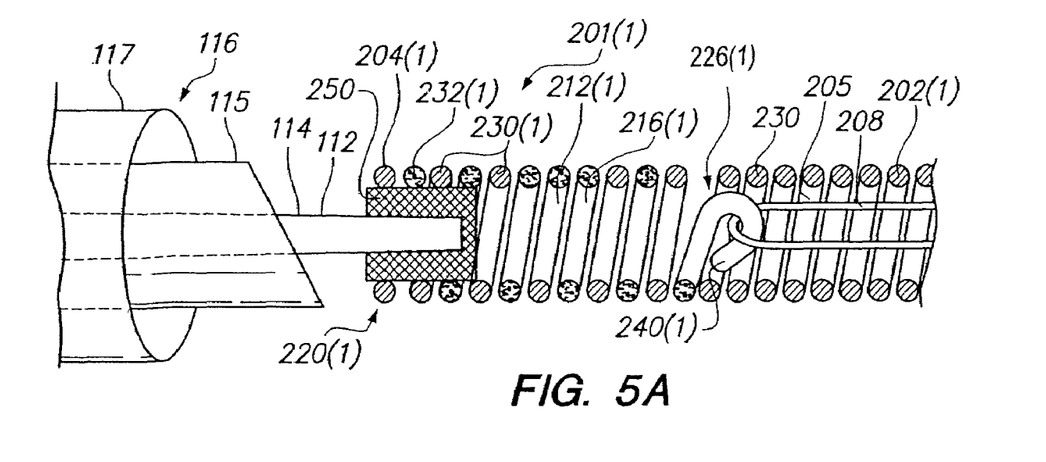
FIG. 5A shows a longitudinal sectional view of the vaso-occlusive assembly of FIG. 3, particularly showing one embodiment of an anchor assembly constructed in accordance with the present inventions.
Figure 5B:
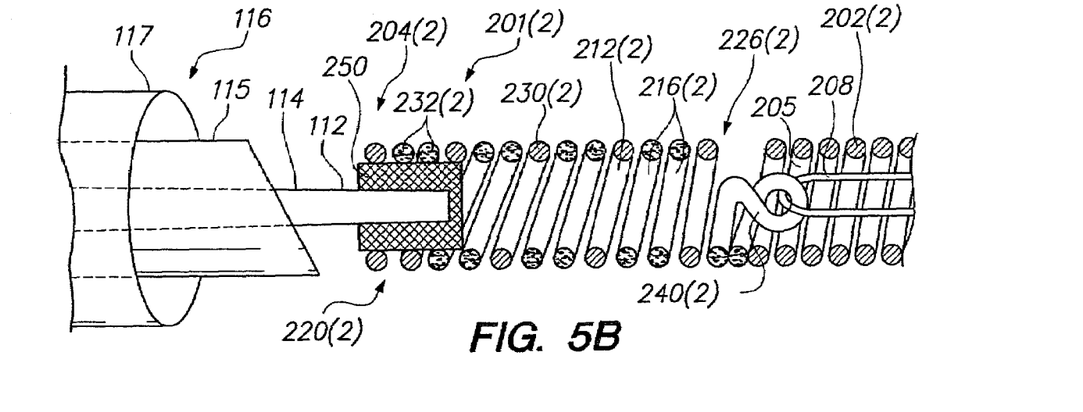
FIG. 5B shows a longitudinal sectional view of the vaso-occlusive assembly of FIG. 3, particularly showing another embodiment of an anchor assembly constructed in accordance with the present inventions.

As illustrated in FIGS. 5A and 5B, the anchor coil 232 (shown in alternative embodiments of FIGS. 5A and 5B as 232(1) and 232(2)) is inserted into the proximal end 204 of the primary coil 202 (shown in alternative embodiments of FIGS. 5A and 5B as 202(1) and 202(2)) by twisting the distal end 240 of the anchor coil 232 into the lumen 205 of the primary coil 202, such that the windings 216 from the anchor coil 232 are situated in the space 214 between adjacent primary coil windings 212. Insertion of the anchor coil 232 can be facilitated by tapering the distal end 226 (shown in alternative embodiments of FIGS. 5A and 5B as 226(1) and 226(2)) of the anchor coil 232. The anchor coil 232 is inserted until the entirety or substantially the entirety of the anchor coil 232 is mated with the proximal end 204 of the primary coil 202.

The loop 240 located at the distal end 226 of the anchor coil 232 is connected to the stretch-resisting member 208. The stretch-resisting member 208 may be attached to the loop 240 through any appropriate means, including looping the stretch-resisting member 208 through or around the loop 240 or tying the stretch-resisting member 208 through or around the loop 240. The attachment of the stretch-resisting member 208 to the loop 240 of the anchor coil 232 fixedly couples the stretch-resisting member 208 to the outer primary coil 202.

The screw mate connection of the anchor coil 232 to the outer primary coil 202 provides additional flexibility at the proximal end, eliminating the "layered coaxial" stiffness of previous anchor assembly designs, by interconnecting the anchor coil 232 with the proximal end 204 of the outer primary coil 202 rather than coaxially situating the anchor coil within the lumen 205 of the primary coil 202.

A filler material 250 is placed within the lumen 205 of the proximal end of the combined anchor coil 232 and primary coil 202 for stabilization and to attach the device 201 to the core wire 114 via detachable means, in this case, an electrolytic joint 112. The filler material 250 preferably comprises a thermoplastic formed into place or an epoxy or the like and adheres in turn to the anchor coil 232, primary coil 202 and the core wire 114. Preferably, the filler material 250 comprises PET, polyamide, silicon, or polyurethane. Alternatively, the filler material 250 may comprise a conductive filler material, such as any alloy, conductive epoxy, or conductive polymer.

Figure 6:
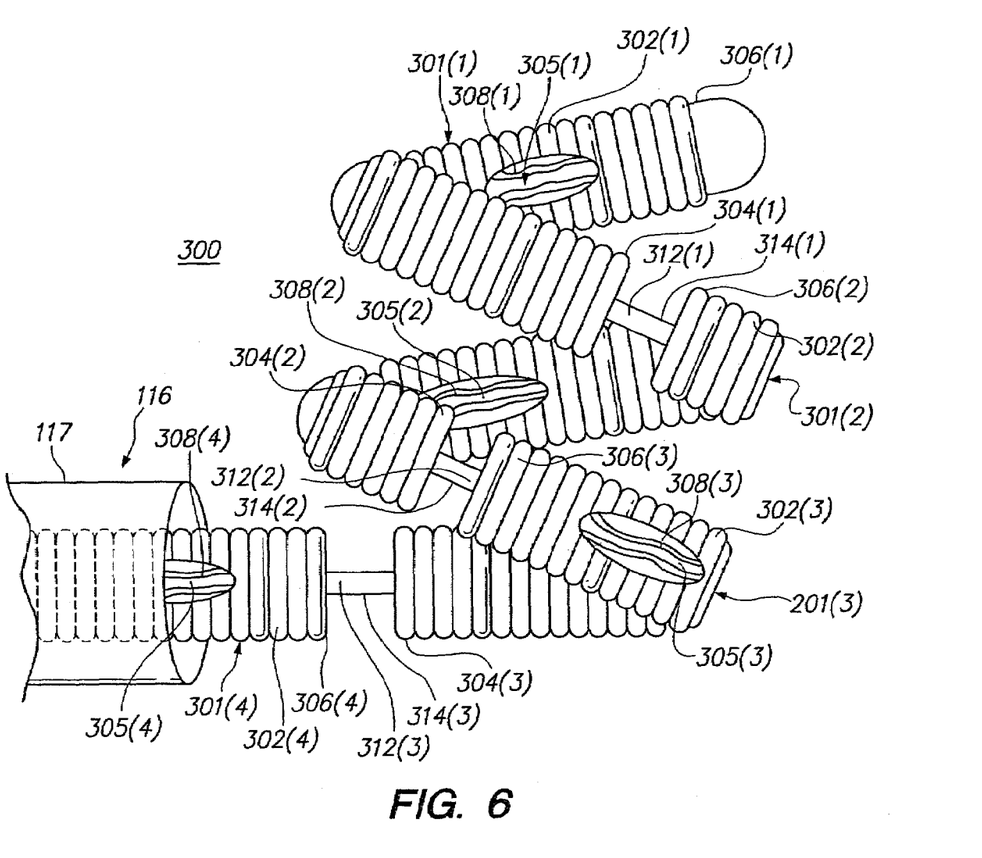
FIG. 6 shows a side view, partial cutaway of a vaso-occlusive assembly constructed in accordance with another preferred embodiment of the present inventions.

Referring to FIG. 6, a vaso-occlusive assembly 300 constructed in accordance with another preferred embodiment is described. The assembly 300 differs from the afore-described vaso-occlusive assemblies 100, 200 in that it includes a vaso-occlusive device 301 with multiple primary coils. For example, four coils 302(1)-(4) are illustrated in FIG. 6, with multiple severable joints 312(1)-(3). Specifically, multiple core wires 314(1)-(3) with electrolytically severable joints 312 are used to detachably connect the coils 302 to each other. Alternatively, the severable joint may be tapered, coated with an insulative polymer and scored, or otherwise modified, such as described in earlier embodiments.

Specifically, the portion of the device 301 that is illustrated includes four outer primary coils 302(1)-(4), each of which has a proximal end 304, a distal end 306, and a lumen 305 extending therethrough. The vaso-occlusive device 301 further includes four stretch-resisting members 308(1)-(4) that extend through each coil lumen 305(1)-(4) and are secured to the respective primary coils 302(1)-(4) at two locations to prevent axial stretching of the primary coils 302(1)-(4). Specifically, the proximal and distal ends of the stretch-resisting members 308 are respectively coupled to the respective proximal and distal ends 304 and 306 of the primary coils 302. Alternatively, the proximal and distal ends of the stretch-resisting members 308 may be coupled to one or more locations between the proximal and distal ends 304 and 306 of the primary coils 302. As will be described in further detail below, a selected number of the primary coils 302 may be released from the delivery device 116 by applying a current to the core wires 114 to dissolve the proximal-most several joint 312 that is exposed to the ionic environment.

The vaso-occlusive device 301 includes an anchor assembly 309 at the proximal end 304 of each of the primary coils 302. The anchor assembly 309 may comprise any of the anchor assemblies discussed above in other preferred embodiments. The vaso-occlusive device 301 may optionally comprise an anchor assembly 309 at the distal end 306 of each of the primary coils 302. Therefore, in each of these segments (with the exception of the primary coil located at the distal end), there are preferably two anchor assemblies coupled to each primary coil at its proximal and distal ends. The stretch-resisting member 308 located in the lumen 305 of the primary coil 302(1) at the distal end may be directly attached to the distal tip of the primary coil 302(1), as discussed previously with respect to vaso-occlusive device 101.

The anchor assemblies 309 and stretch-resisting members 308 can be composed of the same material and constructed in the same manner previously described with respect to the corresponding elements in vaso-occlusive devices 101 and 201. The primary coils of this embodiment are preferably made from conductive material, such as Platinum, stainless steel, and nitinol.

Referring to FIGS. 7A-7E, variations of the anchor assemblies 309(1)-(5) used in the vaso-occlusive assembly 300 are illustrated. For example, the anchor assemblies 309 may include an anchor coil 150 with a distal link 152 (309(1); see FIG. 7A); an anchor chain with multiple links, where a proximal link 172 is twisted and a distal link is either untwisted 174(1) (309(2); see FIG. 7B) or twisted 174(2) (309(3); see FIG. 7C); or an anchor coil 232(1) and 232(2) mated with the primary coil 302(a) and 302(b), such that the windings 216 of the anchor coil 232 are disposed in the space between adjacent windings 212 of the primary coil 302(a) and 302(b) (309(4) and 309(5); see FIGS. 7D and 7E).

Figure 7A:
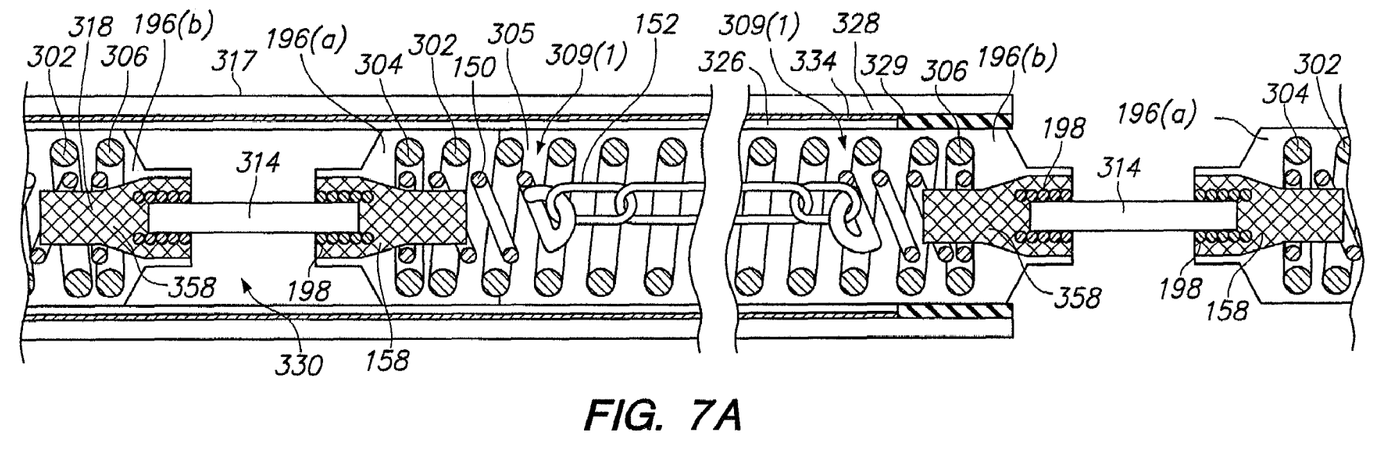
FIGS. 7A-7E show longitudinal sectional views of the vaso-occlusive assembly of FIG. 6, each particularly showing a variation of an anchor assembly.
Figure 7B:
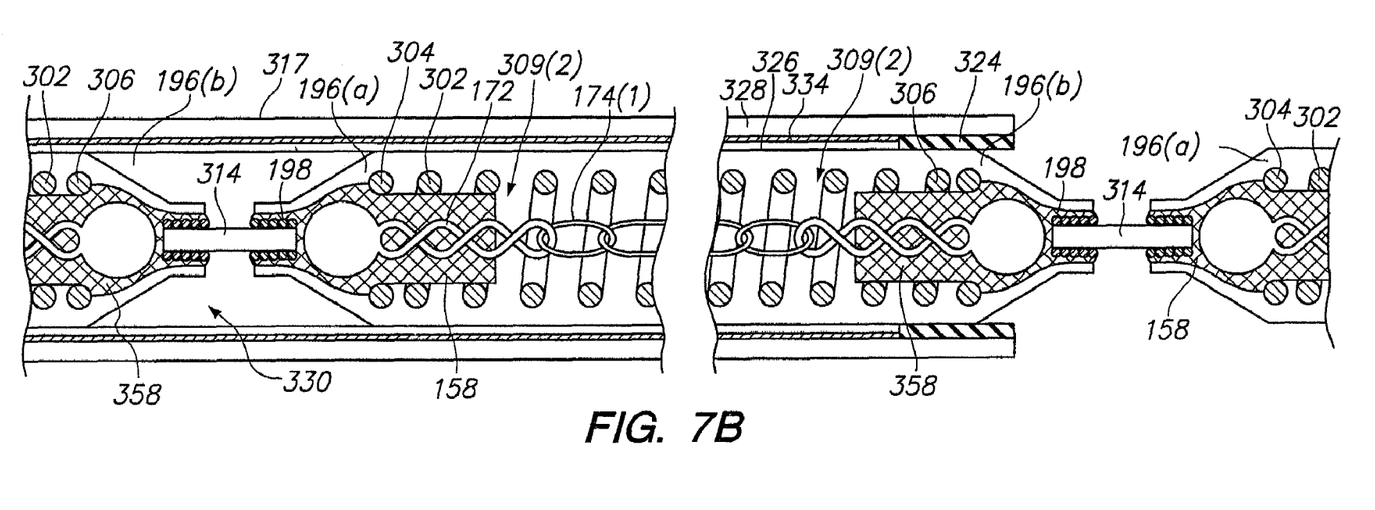
Figure 7C:
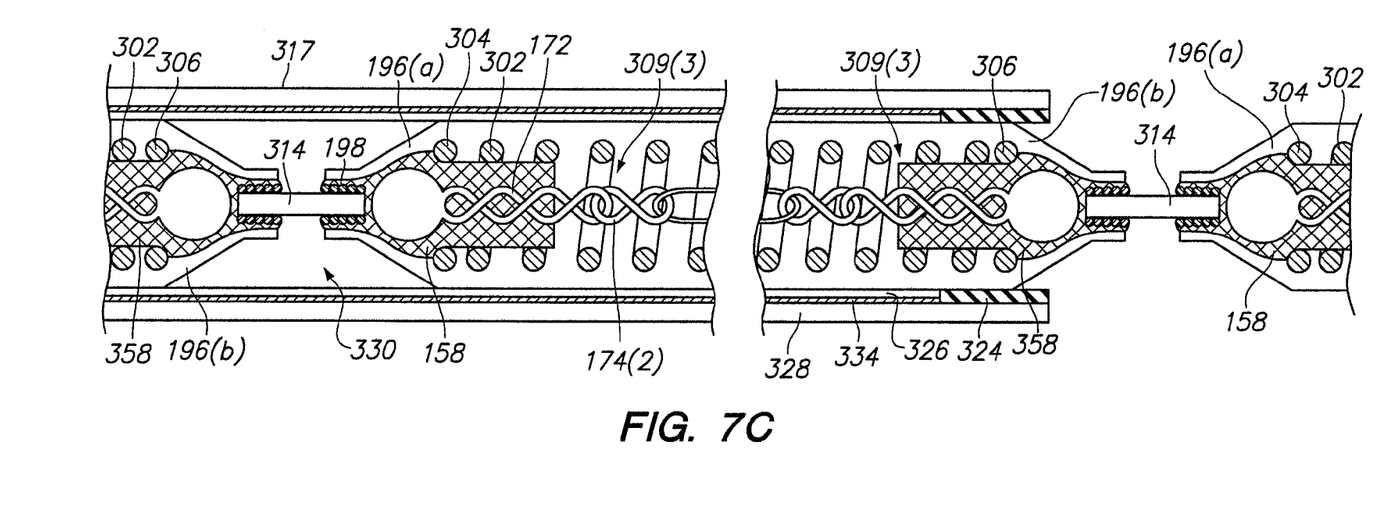

For the embodiments depicted in FIGS. 7A-7C, each primary coil 302 has bushings 196(a) and 196(b) located on its proximal and distal ends 304 and 306 that are used to couple the core wires 314 to the primary coils 302. Specifically, the proximal ends 304 of the primary coils 302 are mounted within the distal ends of the bushings 196(a), and the distal ends of the core wires 314 are disposed within mini coils 198, which in turn, are mounted within the proximal ends of the bushings 196(a). The insulative filler material 158 is placed in the coil lumen 305 of the proximal end 304 of the primary coils 302 for stabilization and to attach the primary coil 302 and anchor assembly 309 to the core wire 314. Similarly, the distal ends 306 of the primary coils 302 are mounted within the proximal ends of the bushings 196(b), and the proximal ends of the core wires 314 are disposed within mini coils 198, which are mounted within the distal ends of the bushings 196(b). A conductive filler material 358 is placed in the coil lumen 305 of the distal end 306 of the primary coils 302 for stabilization and to attach the primary coil 302 and anchor assembly 309 to the core wire 314. As described in a previous embodiment, the mini coil 198 provides additional physical mass obstruction to which the filler materials 158, 358 can adhere, thereby maintaining the tensile strength of the main junctions between the primary coils 302 and the core wires 314.

Figure 7D:
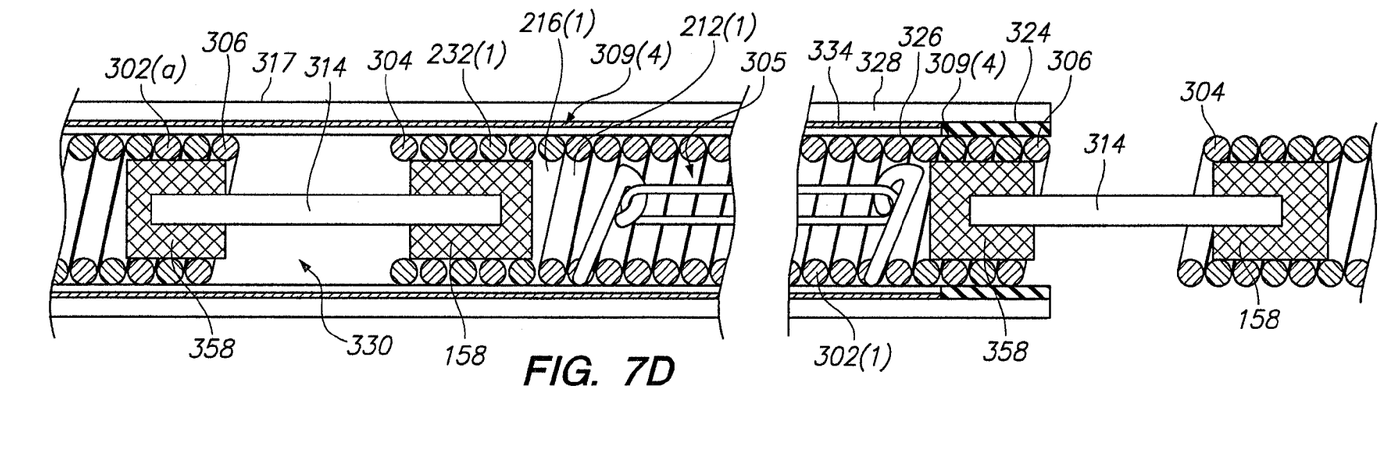
Figure 7E:
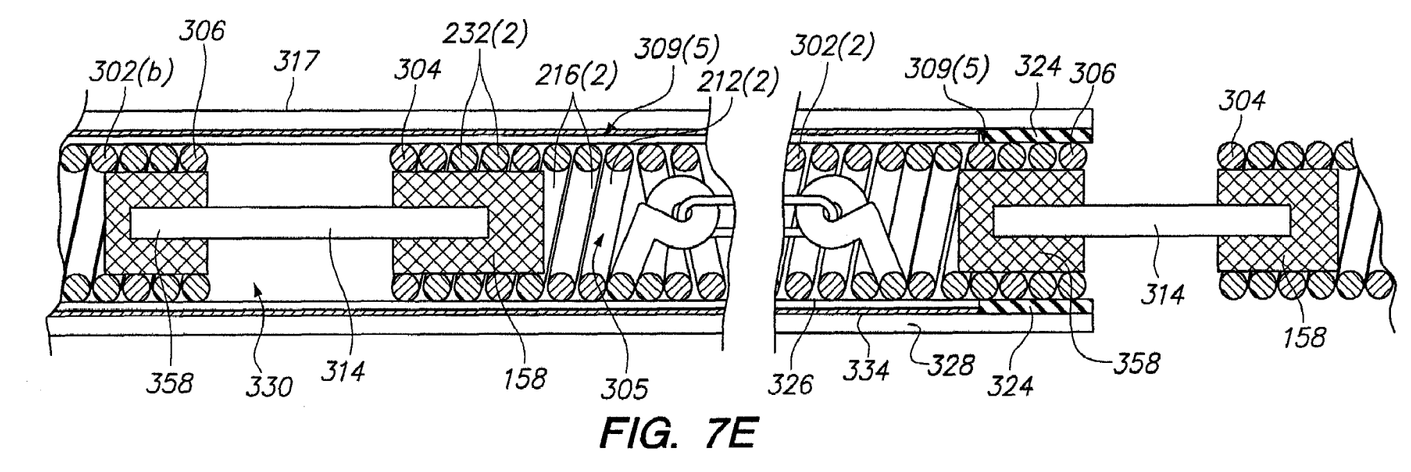

For the embodiments depicted in FIGS. 7D-7E, the core wires 314 are coupled to each primary coil 302(a) and 302(b) without the use of bushings. Specifically, the distal ends of the core wires 314 are held in the coil lumens 305 of the proximal ends 304 of the primary coils 302(a) and 302(b) with the insulative filler material 158. The proximal ends of the core wires are similarly held within the coil lumens 305 of the distal ends 306 of the primary coils 302(a) and 302(b) with a conductive filler material 358.

As previously described, the filler material 158 that connects the distal ends of the primary coils 302 with the proximal ends of the core wires 314 is electrically insulative. Without wishing to be bound by a theory, it is believed that the electrical isolation of the severable joint provided by this insulative filler material 158 prevents or lessens current flow through the outer coils 302 and concentrates current flow through the selected core wire 314. Therefore, the insulative filler material 158 serves two primary functions. The first is to electrically isolate the severable joint 312 so that electrical energy is not transmitted to any part of the assembly 300 distal to the particular link 312 selected for disintegration. In addition, the filler material 158 also serves to reliably and fixedly join the severable joint 312 and the outer coil 302. Preferably, as previously discussed, the insulative filler material 158 comprises a biocompatible, electrically insulative material such as Polyfluorocarbons (e.g., Teflon), PET, polyproplene, polyurethane, polyimides, polyvinylchloride, silicone polymers, and Parylene. Other types of insulative materials are discussed in U.S. Pat. No. 5,941,888, the entirety of which is herein expressly incorporated by reference.

Proximal of the severable joints 312, the electrically conductive filler material 358 joins the distal ends 306 of the outer coils 302 with the proximal ends of the core wires 314. Preferably, as shown in FIGS. 7A-7C, the conductive filler material 358 surrounds the core wire 314 and is contained within the bushing 196(b) and the lumen 305 of the outer coil 302. The conductive filler material 358 provides an electrical pathway between the core wire 314 and the bushing 196(b) and primary coil 302 so that electrical current is readily transmitted to the severable joint 302. Alternatively, as depicted in FIGS. 7D-7E, where there is no bushing, the conductive filler material 358 provides an electrically conductive pathway between the core wire 314 and the outer coil 302. Preferably, the conductive filler material 358 comprises any biocompatible, electrically conductive material, preferably a conductive particle-filled polymer, such as PET with gold flakes, or a suitable metal such as platinum or nitinol, as described in U.S. Pat. No. 5,941,888, the entirety of which has previously been incorporated by reference.

In an alternative embodiment, the core wire 314 is directly connected to the primary coil, which is made from a conductive material (not shown). The conductive joint 370 may be assembled by welding, brazing, soldering, mechanically joining (e.g., crimping) or otherwise appropriate means. Alternatively, the vaso-occlusive device may not contain any insulative filler material, such that the core wires 314 are directly connected to the outer coils 302 at both its proximal and distal ends.

The delivery catheter 317 is preferably equipped with an annular distal electrode 324, partially embedded between a first tube 326 and a second tube 328, as shown in FIG. 7. This electrode functions to convey electrical energy to selected severable joints 314. The electrode 324 can be composed of any conductive biocompatible material. For example the electrode 324 can be comprised of conductive metals and their alloys (for example, steel, titanium, copper, platinum, nitinol, gold, silver or alloys thereof), carbon (fibers or brushes), electrically conductive doped polymers or epoxies, or any combination thereof. In this variation, the electrode 324 and tubes 326 and 328 are preferably designed so that the electrode 324 and catheter lumen 330 present a continuous, non-obstructed, smooth surface to allow vaso-occlusive device to pass smoothly out of the distal end of catheter 317. Such an annular construction maximizes the electrode's exposed surface area so as to increase current flow efficiencies by avoiding too large a current density passing therethrough. In the illustrated embodiment, the distal surface of the electrode 324 is substantially flush with the distal surface of catheter 317. However, other configurations wherein the electrode 324 is spaced inwardly or outwardly from the distal surface of catheter 317 may also be used, as described in U.S. Pat. No. 5,941,888, the entirety of which has previously been incorporated by references. The counter electrode (not shown) may be connected to a needle that is inserted into the patient, e.g., in the groin area. Alternatively, the counter electrode (not shown) may be an adhesive patch electrode attached to the patient's skin.

The catheter 317 further comprises a conductor 334 that is coupled to the electrode 324. The conductor 334, as illustrated in FIG. 7, is in the form of an annular extension of the electrode 324. Alternatively, the conductor 334 can be in the form of a wire or ribbon whose distal end is coupled, e.g., by welding, to the electrode 324. The conductor 334 extends from the electrode 324 between the tubular members 326 and 328 to the proximal end portion of the catheter 317, where it can be electrically connected to a power supply either directly or with a lead, as would be apparent to one of skill in the art. Alternative electrode-catheter arrangements are described in U.S. Pat. No. 5,941,888, the entirety of which has previously been incorporated by reference.

Figure 8A:
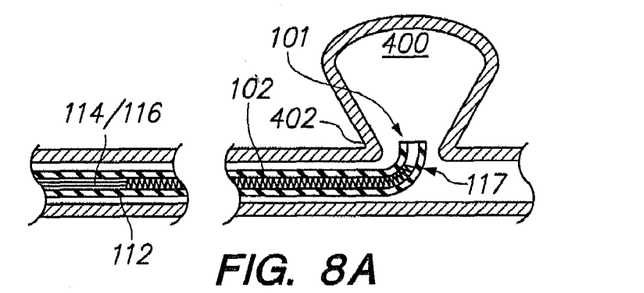
FIGS. 8A-8C show a procedure for delivering the vaso-occlusive assembly of FIG. 1 into an aneurysm.
Figure 8B:
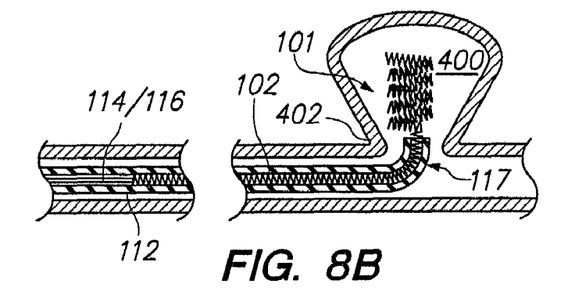
Figure 8C:
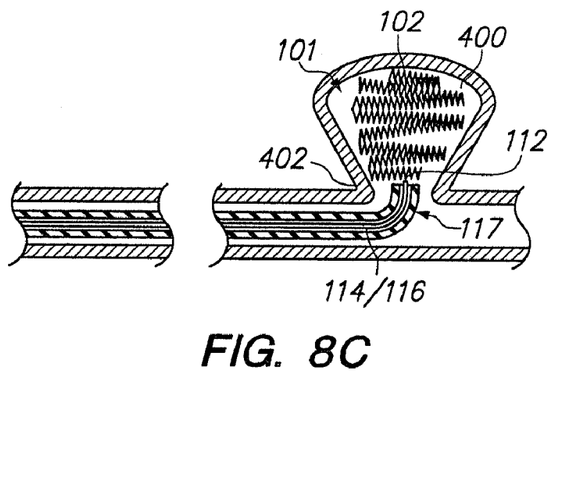

Generally, the vaso-occlusive devices 101 and 201 described above are delivered to an aneurysm within a blood vessel via a delivery catheter 117. Referring to FIGS. 8A-8C, a method of deploying a vaso-occlusive device 101, and in this case, the primary coil 102, to the aneurysm 400 via a delivery catheter 117 is illustrated. The vaso-occlusive device 201 can similarly be delivered to the aneurysm 400 in the foregoing manner, but for the purposes of brevity, only delivery of the vaso-occlusive device 101 will be described in detail.

Turning to FIG. 8A, the catheter 117 is steered to just within a neck 402 of an aneurysm 400. At this point, the primary coil 102 is in its undeployed shape, and is coupled to the core wire 114 via the electrolytically severable joint 112. The vaso-occlusive device 101 extends through the lumen of the delivery catheter 117 such that the primary coil 102 is positioned at the distal end of the delivery catheter 117.

Turning to FIG. 8B, the core wire 114 is then pushed toward the distal end of the catheter 117, causing the primary coil 102 to extend out of the distal end of the catheter 117, through the neck 402, and into the aneurysm 400. As the primary coil 102 is pushed out of the catheter 117, the portion of the primary coil 102 that is free from the constraints of the catheter 117 can assume its deployed shape, e.g., the coil 102 forms a secondary shape such as a cylinder.

Turning now to FIG. 8C, the core wire 114 continues to push the primary coil 102 out of the catheter 117 until the proximal end 104 of the primary coil 102 is deployed within the aneurysm 400. To release the coil 102 from the delivery device 116, a current is applied to the core wire 114, which causes the joint 112 to dissolve, separating the vaso-occlusive device 101 from the proximal end of the delivery device 116. Further discussion of the construction, placement, and other physical details of such electrolytically severable joints may be found in U.S. Pat. No. 5,122,136 to Guglielmi et al.; U.S. Pat. No. 5,354,295 to Guglielmi et al.; and U.S. Pat. No. 5,624,449 to Pham et al.

Depending on constraints such as the condition and size of the aneurysm, the physician may desire to use vaso-occlusive coils of varying length. Instead of having to deploy numerous coils into the aneurysm, a vaso-occlusive device with multiple primary coils connected via multiple detachment sites allows the physician to vary the length of the vaso-occlusive device as needed.

Figure 9A:
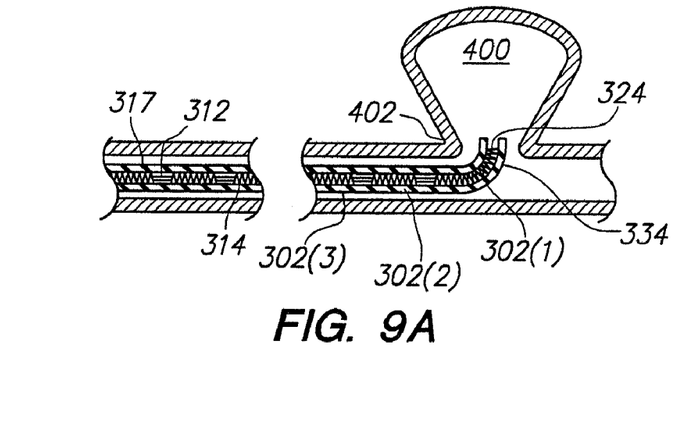
FIGS. 9A-9C show a procedure for delivering the vaso-occlusive assembly of FIG. 6 into an aneurysm.

Turning to FIG. 9A, where the vaso-occlusive assembly 300 contains multiple detachment points 312, the catheter 317 is steered to just within the neck 402 of the aneurysm 400, as described previously. At this point, the multiple primary coils 302 are in their undeployed shape, and are coupled to core wires 314 via electrolytically severable joints 312. The vaso-occlusive devices extend through the lumen of the delivery catheter 317 such that the primary coil 302(1) is positioned at the distal end of the delivery catheter 317.

Figure 9B:
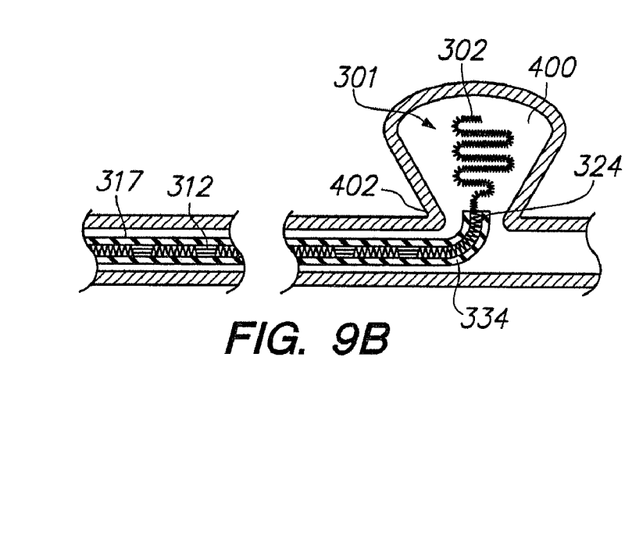

Turning to FIG. 9B, the core wire 314 is then pushed toward the distal end of the catheter 317, causing the primary coil 302(1) to extend out of the distal end of the catheter 317 through the neck 402, and into the aneurysm 400. As the primary coil 302 is pushed from the catheter 317, the portion of the primary coil 302 that is free from the constraints of the catheter 317 can assume its deployed shape.

Figure 9C:
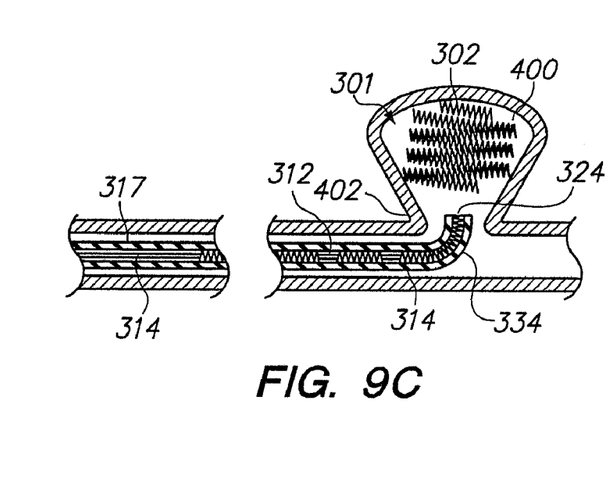

Turning now to FIG. 9C, when the physician has determined that the aneurysm 400 is sufficiently filled with vaso-occlusive device 301 (usually using visualization techniques that are well known in the art), the vaso-occlusive device 301 may be detached from the delivery device 316. To release the desired number of devices 301 from the delivery device 316, the physician positions the device such that the desired severable joint 314 is positioned just distal of the distal end of the catheter 317, and thus, the annular electrode 324. A current is applied to the core wire 314 via the conductor 334 and the electrode 324, which is in contact with the conductive bushing 196(b) or conductive outer coil 302(1) and 302(2). This causes the proximal-most severable joint 312 that is exposed to the ionic environment to dissolve, separating the vaso-occlusive device 301 from the delivery device 316.

Where the core wires 314 are directly coupled to the outer coils 302 with no insulative joints, there are multiple severable joints 312 in this embodiment that are exposed to an ionic environment in the aneurysm 400. The proximal-most severable joint 312 that is exposed to the ionic environment, however, will preferably dissolve first. Presumably, this is because it is closest to the power source and will receive the most current. Other methods of detachment are described in U.S. Pat. No. 5,941,888, the entirety of which has previously been incorporated by reference.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A vaso-occlusive device, comprising:
   a primary coil having a proximal end, a distal end, and a lumen, the primary coil comprising windings;
   a stretch-resisting member extending through at least a portion of the coil lumen and being coupled to the primary coil; and
   an anchor assembly fixedly coupled with the primary coil, the anchor assembly comprising an anchor coil having windings inter-wound between the primary coil windings, wherein the primary coil and anchor coil have approximately the same diameter.

2. The device of claim 1, wherein the anchor coil is directly attached to the stretch-resisting member.

3. The device of claim 1, wherein each winding of the anchor coil is disposed between adjacent windings of the primary coil.

4. The device of claim 1, wherein at least two windings of the anchor coil are disposed between adjacent windings of the primary coil.

5. The device of claim 1, wherein the stretch-resisting member comprises at least one polymeric filament.

6. The device of claim 1, wherein a distal end of the stretch-resisting member is coupled to the distal end of the primary coil and a proximal end of the stretch-resisting member is coupled to the anchor coil.

7. The device of claim 6, wherein the distal end of the stretch-resisting member is directly attached to the distal end of the primary coil.

8. The device of claim 1, wherein the anchor assembly is coupled to the proximal end of the primary coil.

9. The device of claim 1, further comprising a deployment mechanism coupled to the proximal end of the anchor coil.

10. The device of claim 9, wherein the deployment mechanism comprises an electrolytically severable junction adapted to detach from a core wire by imposition of an electrical current on the core wire.

11. The device of claim 1, wherein all of the windings of the anchor coil are disposed between the windings of the primary coil.

12. The device of claim 1, wherein the primary coil is sized to fit within an aneurysm.

13. The device of claim 1, wherein the primary coil windings are spaced, such that a substantial axial stress is not exerted on the primary coil windings and anchor coil windings.

14. The device of claim 1, wherein the anchor coil has a proximal winding, a distal winding, and one or more intermediate windings between the proximal and distal windings, and wherein no portion of the one or more intermediate anchor coil windings is disposed in the coil lumen.

15. The device of claim 1, wherein the anchor coil is approximately 2 mm long.

16. A catheter assembly for occluding a body cavity comprising:
   a delivery device having a distal end; and
   a vaso-occlusive device associated with the distal end of the delivery device, the vaso-occlusive device comprising:
   a primary coil having a proximal end, a distal end, and a lumen, the primary coil comprising windings;
   a stretch-resisting member extending through at least a portion of the coil lumen and being coupled to the primary coil; and
   an anchor assembly fixedly coupled with the primary coil, the anchor assembly comprising an anchor coil having windings inter-wound between the primary coil windings, wherein the primary coil and anchor coil have approximately the same diameter.

17. The catheter assembly of claim 16, wherein the anchor coil is directly attached to the stretch-resisting member.

18. The catheter assembly of claim 16, wherein each winding of the anchor coil is disposed between adjacent windings of the primary coil.

19. The catheter assembly of claim 16, wherein at least two windings of the anchor coil are disposed between adjacent windings of the primary coil.

20. The catheter assembly of claim 16, wherein the stretch-resisting member comprises at least one polymeric filament.

21. The catheter assembly of claim 16, wherein a distal end of the stretch-resisting member is coupled to the distal end of the primary coil and a proximal end of the stretch-resisting member is coupled to the anchor coil.

22. The catheter assembly of claim 21, wherein the distal end of the stretch-resisting member is directly attached to the distal end of the primary coil.

23. The catheter assembly of claim 16, wherein the anchor assembly is coupled to the proximal end of the primary coil.

24. The catheter assembly of claim 16, wherein the vaso-occlusive coil is detachably connected via an electrolytic joint.

25. The catheter assembly of claim 16, wherein the body cavity comprises an aneurysm.

26. The catheter assembly of claim 16, further comprising a catheter, wherein the delivery device is a core wire slidably disposed within the catheter, wherein the vaso-occlusive device is detachably coupled to the core wire.

27. The catheter assembly of claim 16, wherein the primary coil windings are spaced, such that a substantial axial stress is not exerted on the primary coil windings and anchor coil windings.

28. The catheter assembly of claim 16, wherein the anchor coil has a proximal winding, a distal winding, and one or more intermediate windings between the proximal and distal windings, and wherein no portion of the one or more intermediate anchor coil windings is disposed in the coil lumen.

29. The catheter assembly of claim 16, wherein the anchor coil is approximately 2 mm long.

* * * * *